United States Patent [19]

Nakajima et al.

[11] Patent Number: 4,787,966
[45] Date of Patent: Nov. 29, 1988

[54] OXYGEN CONCENTRATION SENSOR FOR AN INTERNAL COMBUSTION ENGINE

[75] Inventors: Toyohei Nakajima; Yasushi Okada; Toshiyuki Mieno; Nobuyuki Cono, all of Wako, Japan

[73] Assignee: Honda Giken Kogyo Kabushiki Kaisha, Tokyo, Japan

[21] Appl. No.: 71,961

[22] Filed: Jul. 10, 1987

[30] Foreign Application Priority Data

Jul. 14, 1986 [JP] Japan ................... 61-165329

[51] Int. Cl.$^4$ ........................................... G01N 27/58
[52] U.S. Cl. .................................... 204/406; 204/410; 204/412; 204/425
[58] Field of Search ............... 204/406, 410, 412, 425, 204/1 S; 123/489

[56] References Cited

U.S. PATENT DOCUMENTS 4,272,329  6/1981  Hetrick et al. ................ 204/1 T
4,707,241  11/1987  Nakagawa et al. ............ 204/406

Primary Examiner—G. L. Kaplan
Attorney, Agent, or Firm—Pollock, VandeSande & Priddy

[57] ABSTRACT

An oxygen concentration sensor having an oxygen ion conductive solid electrolyte member forming a gas diffusion restricted region into which a measuring gas is introduced, includes a pump current source for supplying a pump current across a pair of electrodes sandwiching the solid electrolyte through a current detection element and a heater for heating the solid electrolyte. By an arrangement in which the current detection element is connected to one of the pair of electrodes facing the gas diffusion restricted region, error of measurement due to leakage of a drive current of the heater is prevented.

3 Claims, 4 Drawing Sheets

OXYGEN CONCENTRATION SENSOR FOR AN INTERNAL COMBUSTION ENGINE

BACKGROUND OF THE INVENTION

1. Field of the Invention

The present invention relates to an oxygen concentration sensor for an internal combustion engine.

2. Description of Background Information

Systems for controlling the air/fuel ratio by feedback operation have been developed, in which oxygen concentration in the exhaust gas of the engine is detected by an oxygen concentration sensor and the air/fuel ratio of mixture to be supplied to the engine is feedback controlled to a target value in response to an output signal level of the $O_2$ sensor for the purpose of purifying the exhaust gas and improving the fuel economy.

In such an air/fuel ratio control system, there is a type of oxygen concentration sensor which is capable of producing an output signal whose level is proportional to the oxygen concentration in the exhaust gas of the engine. As an example, Japanese Patent Application laid open No. 59-192955 discloses an oxygen concentration sensor which includes a pair of flat oxygen ion conductive solid electrolyte members each of which is provided with a pair of electrodes, and arranged so that the measuring gas is retained in the proximity of the surface of one of electrodes provided on one of said pair of solid electrolyte members, and the surface of the other electrode provided on that one of two solid electrolyte members faces an atmospheric air.

In this oxygen concentration sensor, one of the two oxygen ion conductive solid electrolyte members and the electrode pair operate as an oxygen concentration ratio detection sensor cell element, and the other one of two oxygen ion conductive solid electrolyte members and the electrode pair operate as the oxygen pump element. By supplying a current so to cause the oxygen ions to move through the inside of the oxygen pump element toward the electrode located on the side of the retained measuring gas when the voltage generated across the electrodes of the oxygen concentration ratio detection sensor cell element is higher than a reference voltage, and to cause the oxygen ions to move through the inside of the oxygen pump element toward the electrode located on the other side of the retained measuring gas when the voltage generated across the oxygen concentration ratio detection sensor cell element is equal to or lower than the reference voltage, the pump current value becomes proportional to the oxygen concentration (air/fuel ratio) both in the lean and rich regions. FIG. 1 shows an example of the pump current $I_P$ which varies in proportion to the oxygen concentration. This pump current $I_P$ is in general detected in the form of a voltage generated across the terminals of a current detection resistor which is provided in series with the oxygen pump element.

Furthermore, in this type of oxygen concentration sensor, a desirable characteristic of proportional oxygen concentration detection is obtained only when the temperature of the oxygen pump element and the sensor cell element are raised quite high. Therefore, a heater element fixed on the oxygen ion conductive solid electrolyte is generally used, so that the oxygen pump element and the sensor cell element are heated by the heater element. In the normal structure, one of the electrodes of the oxygen pump element is grounded and the voltage is applied to the other electrode through the current detection resistor. In this structure, the heater element is supplied with a heater current. However, there is a problem of a part of the heater current supplied to the heater element flowing into the oxygen pump element by leakage this in addition to the pump current normally supplied to the oxygen pump element. This leakage of the pump current influences the amount of moving ions. Therefore, from the voltage across the terminals of the current detection resistor under such a condition, it is difficult to accurately detect the pump current value, i.e. the oxygen concentration in the measuring gas.

SUMMARY OF THE INVENTION

An object of the present invention is therefore to provide an oxygen concentration sensor in which measures are taken to detect the pump current value including the current caused by the leakage of the heater current, so that the accuracy of the detection of the oxygen concentration in the measuring gas is very much improved.

An oxygen concentration sensor according to the present invention is characterized by an arrangement in which the current detection element is connected, in the above mentioned structure, to one of the electrodes of the oxygen pump element facing the measuring gas, thereby preventing the error of oxygen concentration measurement error due to the leakage current from the current from supplied to the heater element.

DETAILED DESCRIPTION OF PREFERRED EMBODIMENTS

Referring to the accompanying drawings, an embodiment of the present invention is explained hereinbelow.

Figure 1:
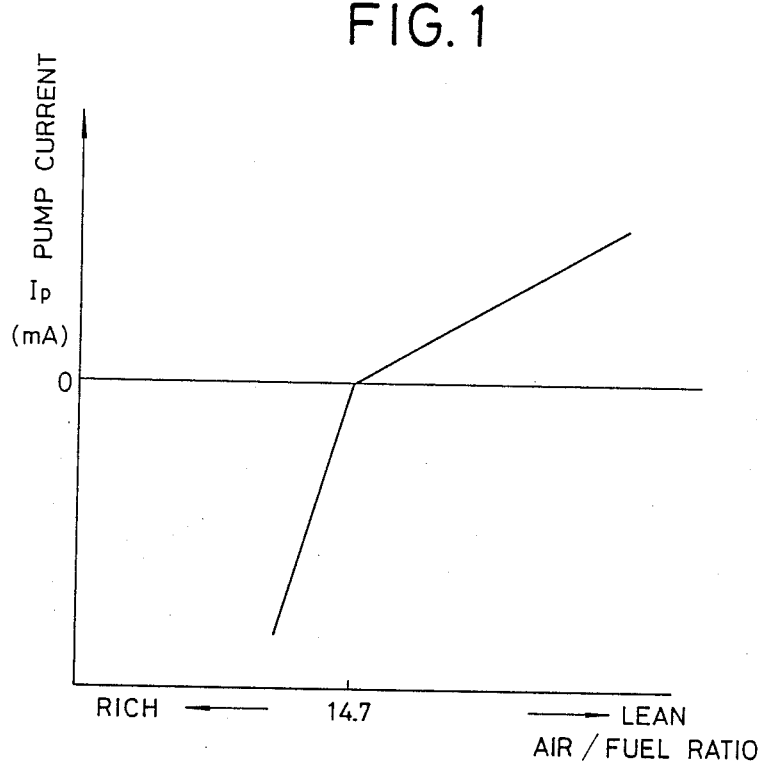
FIG. 1 is a diagram showing an example of output signal characteristic of the oxygen concentration sensor.
Figure 2:
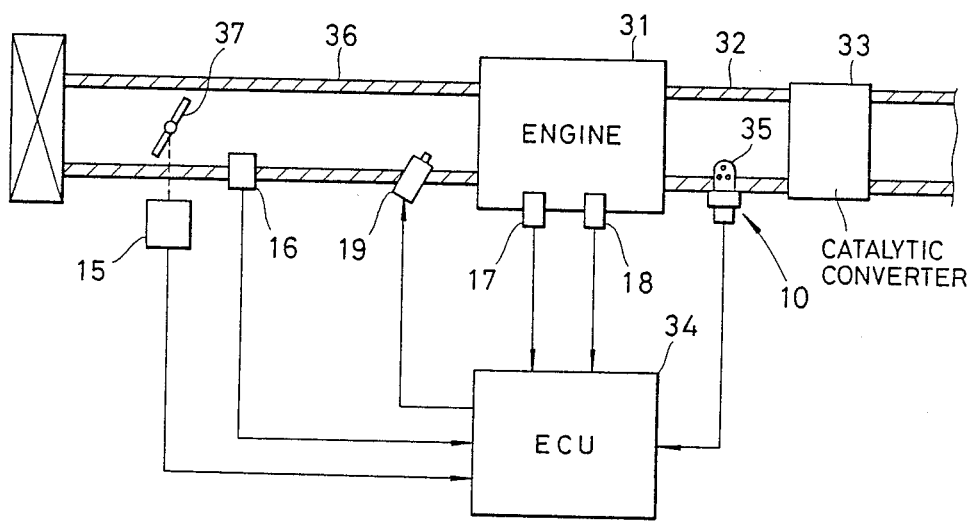
FIG. 2 is a schematic diagram showing the structure of an electronically controlled fuel injection system in which the oxygen concentration sensor according to the present invention is used.

FIG. 2 illustrates an electronically controlled fuel injection system of an internal combustion engine which is provided with the oxygen concentration sensor according to the present invention. In this system, a detection part 10 of the oxygen concentration sensor is disposed in an exhaust gas passage 32 of an internal combustion engine 31, on the upstream side of a three-way catalytic converter 33. A detection output signal of the detection part 10 of the oxygen concentration sensor is supplied to an ECU (electronic control unit) 34.

Figure 3:
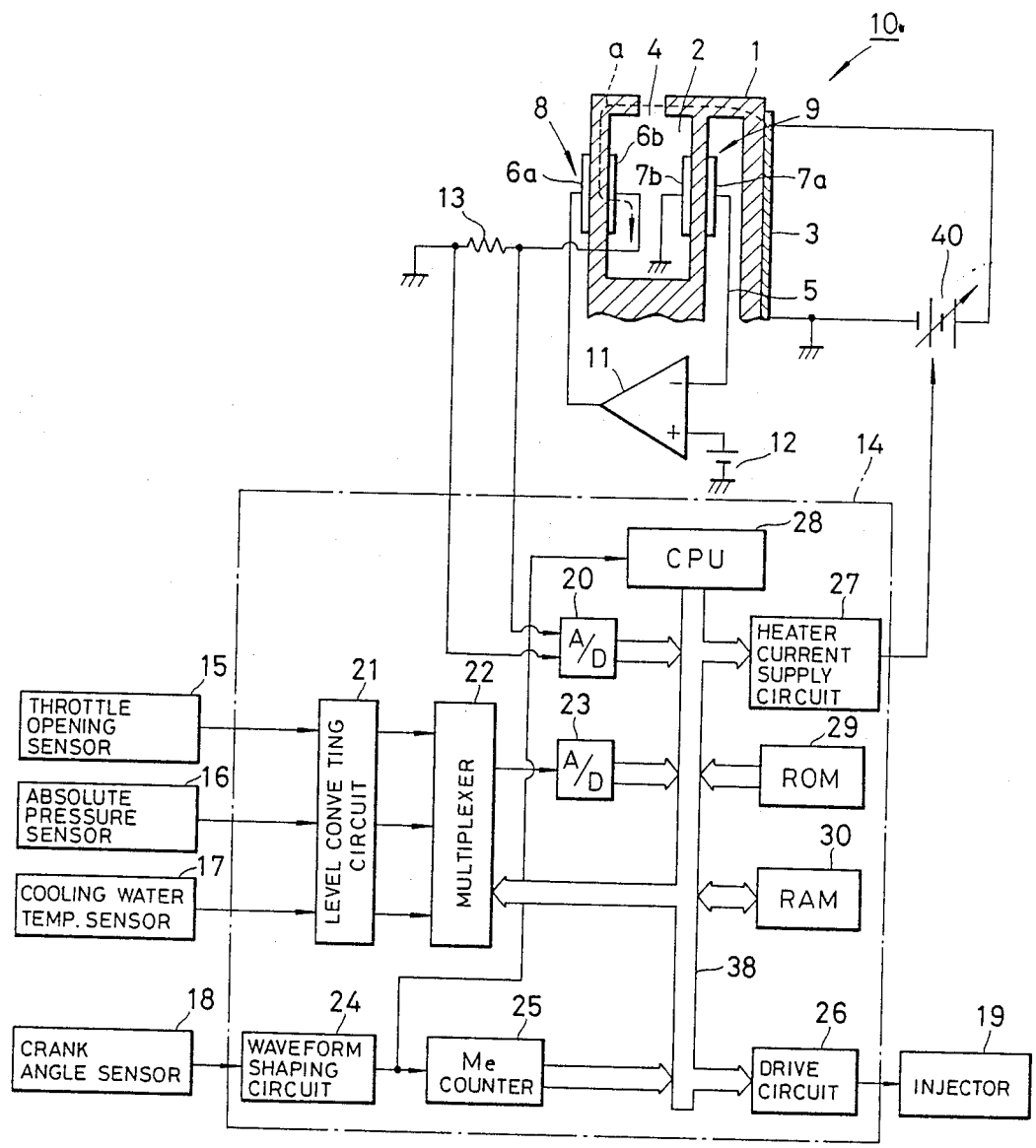
FIG. 3 is a block diagram showing the construction of the detection part of the oxygen concentration sensor and the electronic control unit utilized in the system of FIG. 2.

In a protection case 35 of the detection part 10 of the oxygen concentration sensor, there is provided an oxygen ion conductive solid electrolyte member 1 having a generally cubic configuration as shown in FIG. 3. In the oxygen ion conductive solid electrolyte member 1, a gas retaining chamber 2 is formed. The gas retaining chamber 2 leads to the outside of the oxygen ion conductive solid electrolyte member 1 through a gas introduction hole 4 for introducing the measuring gas, i.e. the exhaust gas of the engine. The gas introduction hole 4 is positioned in an exhaust gas passage 32 so that the exhaust gas can easily flow into the gas retaining chamber 2. The oxygen-ion conductive solid electrolyte member 1 is provided with a reference atmospheric air chamber 5 into which atmospheric air is introduced, in such a manner that the reference atmospheric air chamber 5 is separated from the gas retaining chambers 2 by means of a partition wall between them. In the partition wall between the gas retaining chamber 2 and the reference atmospheric air chamber 5, and in the wall of the gas retaining chamber 2 on the opposite side of the atmospheric air chamber 5, there are two pairs of electrodes 7a and 7b, and 6a and 6b, respectively. The solid electrolyte member 1 and the pair of electrodes 6a and 6b together operate as an oxygen pump element 8. On the other hand, the solid electrolyte member 1 and the pair of electrodes 7a and 7b together operate as a sensor cell element 9. Further, a heater element 3 is provided on an outer wall of the reference atmospheric air chamber 5. For the oxygen ion conductive solid electrolyte member 1, zirconium dioxide ($ZrO_2$) is suitably used, and platinium (Pt) is used as the electrodes 6a, 6b, 7a and 7b.

The electronic control unit 34 includes a differential amplifier 11, a reference voltage source 12, a current detection resistor 13 and a control circuit 14. The electrode 6a of the oxygen pump element 8 in the detection part 10 is connected to an output terminal of the differential amplifier 11, and the electrode 6b is grounded through the current detection resistor 13. The electrode 7b of the sensor cell element 9 is grounded and the electrode 7a is connected to an inverting input terminal of the differential amplifier 11. The differential amplifier 11 produces an output voltage corresponding to the difference between a voltage generated across the electrodes 7a and 7b of the sensor cell element 9, and a reference voltage Vr supplied from the reference voltage source 12 to a noninverting input terminal thereof. The output voltage of the differential amplifier 11 is supplied to a series circuit formed by the electrodes 6a and 6b and the current detection resistor 13. The reference voltage Vr generated by the reference voltage source 12 is set at a level (0.4 V for example) corresponding to the stoichiometric air/fuel ratio. Terminals of the current detection resistor 13 operate as output terminals of the oxygen concentration sensor, and a voltage derived across the terminals of the current detection resistor 13 is supplied to the control circuit 14 as an oxygen concentration detection value.

To the control circuit 14, there are connected output signals from a throttle opening sensor 15 which comprises a potentiometer and generates an output voltage whose level corresponds to the opening of a throttle valve 37, an absolute pressure sensor 16 provided in an intake pipe 36, on the downstream side of the throttle valve 37, which generates an output signal whose level corresponds to the absolute pressure in the intake pipe 36, a cooling water temperature sensor 17 for generating an output voltage whose level corresponds to the cooling water temperature of the engine, and a crank angle sensor 18 for generating a pulse train signal in synchronism with the rotation of the crankshaft (not shown) of the engine.

The control circuit 14 includes an A/D (analog to digital) converter 20 having differential inputs which converts the voltage across the terminals of the current detection resistor 13 to a digital signal, a level converting circuit 21 for performing the level conversion of the output signals of the throttle opening sensor 15, the absolute pressure sensor 16, and the water temperature sensor 17, a multiplexer 22 for selectively outputting one of the output signals of the sensors through the level converting circuit 21, an A/D converter 23 for converting the signal supplied from the multiplexer 22 into a digital signal, a waveform shaping circuit 24 for performing the waveform shaping of the output signal of the crank angle sensor 18 and outputting it as a pulse signal such as a TDC signal, a counter 25 for detecting the interval of the TDC signal outputted by the waveform shaping circuit 24 by counting the number of clock pulses supplied from a clock pulse generating circuit (not shown), a drive circuit 26 for driving an injector 19, a heater current supply circuit 27 for supplying a drive current of the heater element 3, a CPU (central processing unit) 28 for executing digital operations, for example, according to various operation programs and data previously stored in a ROM 29 and a RAM 30.

The injector 19 is provided on the intake pipe 36 of the engine 31 near intake valves (not shown). The heater element is supplied with a voltage from a heater power source 40 and the output voltage of the heater power source 40 is controlled by the heater current supply circuit 27. By applying the voltage to the heater element 3, heat is generated at the heater element 3, and the oxygen pump element 8 and the sensor cell element 9 are heated to a suitable temperature which is higher than the temperature of exhaust gas.

With this arrangement, data indicative of the pump current $I_P$ flowing through the oxygen pump element 8 from the A/D converter 20, information of the throttle opening $\theta$th, the absolute pressure $P_{Ba}$ in the intake pipe, the cooling water temperature $T_W$ selectively from the A/D converter 23 and information of the count value in the intrval of generation of the rotation pulses from the counter 25 are supplied to the CPU 28 through an input/output bus 38. The CPU 28 reads the above-mentioned various information in accordance with the program stored in the ROM 29 and calculates a fuel injection time $T_{OUT}$ of the injector 19 corresponding to the amount of the fuel to be supplied to the engine 31 using a calculation formula described later, in response to these information in a fuel supply routine synchronized with the TDC signal. The fuel injector 19 is actuated by the drive circuit 26 only for the fuel injection time $T_{OUT}$ so as to supply the fuel to the engine 31.

The fuel injection time $T_{OUT}$ is, for example, calculated by the following formula:

$$T_{OUT} = T_i \times K_{O2} \times K_{WOT} \times K_{TW} \quad (1)$$

where $T_i$ represents a basic supply amount determined by the engine rotational speed Ne and the pressure $P_{BA}$ in the intake passage, $K_{O2}$ represents a feedback correction coefficient of the air/fuel ratio which is determined in accordance with the output signal level of the oxygen concentration sensor, $K_{WOT}$ represents a fuel increment correction coefficient for a high load operation, and $K_{TW}$ represents a coefficient of the engine coolant temperature. The values of $T_i$, $K_{O2}$, $K_{WOT}$, and $K_{TW}$ are set in subroutines of the fuel supply routine.

When the supply of the pump current to the oxygen pump element 8 is started, a voltage developing across the electrodes 7a and 7b of the sensor cell element 9 becomes lower than the reference voltage generated by the reference voltage source 2 if the air/fuel ratio of the mixture supplied to the engine 31 is in the lean region. Therefore, the differential amplifier 11 produces a positive output signal. This positive output signal is supplied to the electrode 6a of the oxygen pump element 8. Since the pump current flows from the electrode 6a to the electrode 6b of the oxygen pump element 8, oxygen in the gas retaining chamber 2 is ionized at the electrode 6b, and moves through the inside of the oxygen pump element 8, and released in the form of oxygen gas at the electrode 6a. The oxygen in the gas retaining chamber 2 is pumped out in this way.

By the pumping of the oxygen in the gas retaining chamber 2, a difference of oxygen concentration develops between the exhaust gas in the gas retaining chamber 2 and the atmospheric air in the reference atmospheric air chamber 5. A voltage Vs corresponding to this difference of oxygen concentration develops across the electrodes 7a and 7b of the sensor cell element 9, and this voltage Vs is supplied to the inverting input terminal of the differential amplifier 11, where the output voltage of the differential amplifier 11 has a voltage proportional to the difference between the voltage Vs and the reference voltage Vr. And this output voltage is supplied to the series circuit of the oxygen pump element and the current detection resistor 13.

On the other hand, the voltage Vs exceeds the output voltage of the reference voltage source when the air/fuel ratio of the mixture is in the rich region. Therefore, the output signal level of the differential amplifier 11 changes from the positive level to the negative level. By this negative level output signal, the direction of the pump current flowing across the electrodes 6a and 6b of the oxygen pump element 8 is turned over. Under this condition, the pump current flows from the electrode 6b to the electrode 6a, and oxygen in the outside is ionized at the electrode 6a, and moves through the inside of the oxygen pump element 8 to the electrode 6b where the oxygen ion is released into the gas retaining chamber 2 in the form of oxygen gas. In this way, the oxygen is pumped into the gas retaining chamber 2.

The leakage of the heater current to be supplied to the heater element will be explained. When the air/fuel ratio is in the lean region, a part of the heater current 3 supplied from the heater power source 40 is, as shown by the broken line a in FIG. 3, flows from the heater element through the solid electrolyte member 1, and reaches a portion between the electrodes 6a and 6b of the oxygen pump element 8. This leakage current is combined with the pump current generated by the positive output signal level of the differential amplifier 11, and flows toward the electrode 6b, and further flows into the ground through the current detection resistor 13.

Also by this leakage current, the oxygen in the gas retaining chamber 2 is pumped out, and the voltage is generated across the electrodes 7a and 7b of the sensor cell element accordingly, by which the output voltage of the differential amplifier 11 is controlled. Therefore, a voltage representing the pump current including the leakage current from the current detection resistor 13 is supplied to the control circuit 14 as the oxygen concentration detection value.

Figure 4:
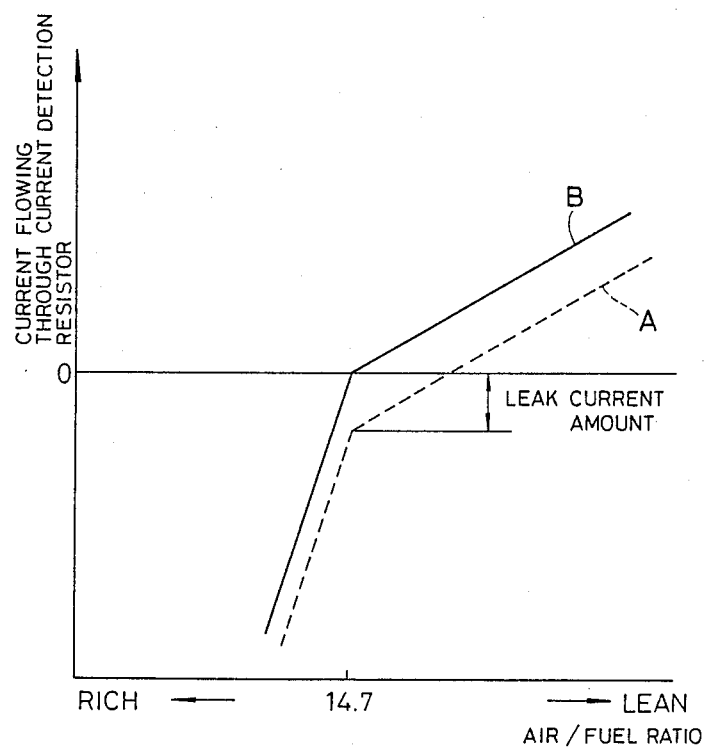
FIG. 4 is a diagram showing the output signal characteristic of the oxygen concentration sensor used in the system of FIG. 2.

FIG. 4 shows an output signal characteristic of the oxygen concentration sensor according to the present invention, in which the broken line A shows the current flowing through the oxygen pump element 8 by means of the output voltage of the differential amplifier 11, i.e., the current detected as the pump current value in the conventional arrangement by means of the current detection resistor. On the other hand, the characteristic shown by the solid line B represents the pump current including the leakage current which is detected by means of the current detection resistor 13.

When the air/fuel ratio is in the rich region, the leakage current of the heater current supplied to the heater element 3 from the heater power source 40 flows into the electrode 6b and the current detection resistor 13, to decrease the pump current. Therefore, te voltage representing the pump current obtained by subtracting the leakage current from the current generated by the output voltage of the differential amplifier is supplied to the control circuit 14 as the oxygen concentration detection value.

Therefore, even if the leakage of the heater current occurs, the pump current including the leakage current flows through the oxygen pump element 8 to pump in or out the oxygen so that the oxygen in the gas retaining chamber is maintained constant, i.e., the state of equlibration is attained.

Therefore, the pump current $I_P$ detected by means of the current detection resistor 13 becomes proportional to the oxygen concentration in the exhaust gas both in the lean region and in the rich region. In accordance with this pump current value $I_P$, the above mentioned feedback correction coefficient $KO_2$ is determined.

Figure 5:
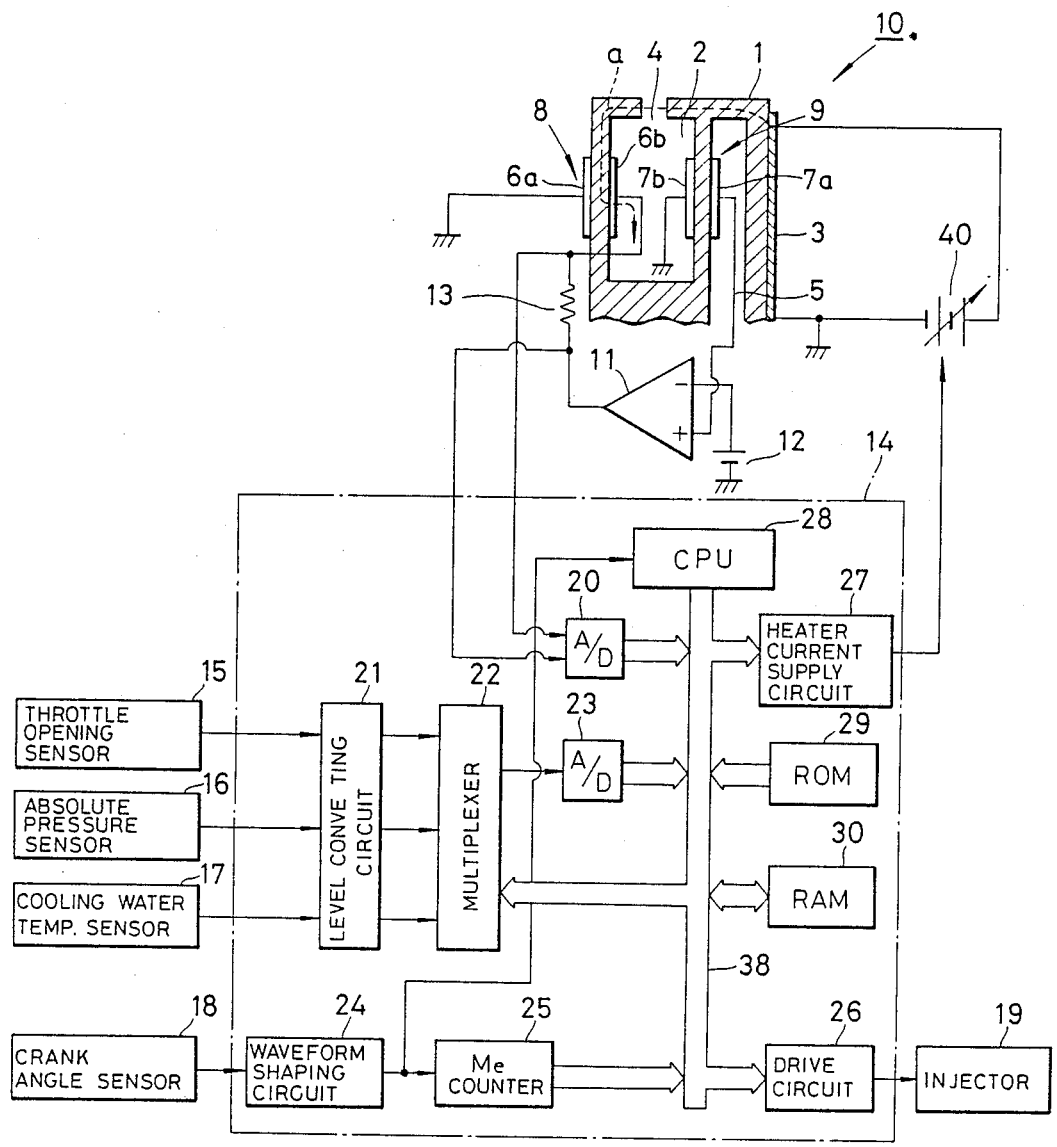
FIG. 5 is a block diagram showing a second embodiment of the oxygen concentration sensor according to the present invention.

Referring to FIG. 5, the second embodiment of the present invention will be explained.

As shown, the electrode 6a of the oxygen pump element 8 is grounded and the electrode 6b located in the gas retaining chamber 2 is connected to the output terminal of the differential amplifier 11 through the current detection resistor 13. With this arrangement, the pump current from the differential amplifier 11 flows through the oxygen pump element 8 in the reverse direction with respect to the embodiment of FIG. 3. Therefore, the electrode 7a of the sensor cell element 9 is connected to the noninverting input terminal of the differential amplifier 11 and the inverting input terminal of the differential amplifier 11 is connected to the reference voltage source 12. In this embodiment, the leak current of the heater current which may flow through the electrode 6b flows through the current detection resistor 13 as in the case of the previous embodiment.

It will be appreciated from the foregoing, according to the present invention, the current detection resistor inserted in the circuit for supplying the pump current is connected to the electrode of the oxygen pump element located on the gas retaining chamber's side. Therefore, all of the current flowing through this electrode of the oxygen pump element including the leak current of the heater current is detected by means of the current detection resistor. Thus, the oxygen concentration value is detected accurately, and the accuracy of the air/fuel ratio control is improved by controlling the air/fuel ratio of the mixture supplied to the engine in accordance with the this detection value of the oxygen concentration.

What is claimed is:

1. An oxygen concentration sensor, comprising:
   an oxygen ion conductive solid electrolyte member forming a gas diffusion restricted region into which a measuring gas is introduced;
   a pair of electrodes sandwiching said solid electrolyte member;
   pump current supply means applying a pump voltage to said pair of electrodes through a current detection element to generate a pump current; and
   a heater element connected to said solid electrolyte member for heating said solid electrolyte member when a heater current is supplied from a heater current source;
   wherein said oxygen concentration sensor detects an oxygen concentration in said measuring gas in terms of a current value of said pump current supplied through said current detection element and controls oxygen concentration in said gas diffusion restricted region by conducting oxygen ions through said solid electrolyte member in accordance to the flow of said pump current; and
   wherein said current detection element is connected to the electrode of said pair of electrodes facing said gas diffusion restricted region for insuring that said current value is representative of said pump current and possible leakage current from said heater current.

2. An oxygen concentration sensor as set forth in claim 1, wherein said pump current supply means applies said pump voltage against a ground potential to an outer electrode of said pair of electrodes; and
   wherein said current detection element is a resistor connected between said one of said pair of electrodes and ground.

3. An oxygen concentration sensor as set forth in claim 1, wherein said pump current supply means generates said pump voltage against a ground potential; and
   wherein said current detection element is a resistor connected between said one of said pair of electrodes and said pump current supply means, an outer electrode of said pair of electrodes being connected to ground.

* * * * *

UNITED STATES PATENT AND TRADEMARK OFFICE
CERTIFICATE OF CORRECTION

PATENT NO. : 4,787,966
DATED : November 29, 1988
INVENTOR(S) : Toyohei Nakajima, et al.

It is certified that error appears in the above-identified patent and that said Letters Patent is hereby corrected as shown below:

On the Title Page,
In Section "[75]", the identification of the inventors, change "Nobuyuki Cono" to --Nobuyuki Oono--.

Signed and Sealed this

Second Day of May, 1989

Attest:

DONALD J. QUIGG

Attesting Officer

Commissioner of Patents and Trademarks